(12) United States Patent
Hartley et al.

(10) Patent No.: US 8,449,600 B2
(45) Date of Patent: May 28, 2013

(54) ILIAC EXTENSION WITH FLARED CUFF

(75) Inventors: David Ernest Hartley, Wannanup (AU);
Werner Dieter Ducke, Eight Mile Plains (AU)

(73) Assignee: Cook Medical Technologies LLC, Bloomington, IN (US)

( * ) Notice: Subject to any disclaimer, the term of this patent is extended or adjusted under 35 U.S.C. 154(b) by 107 days.

(21) Appl. No.: 13/211,759

(22) Filed: Aug. 17, 2011

(65) Prior Publication Data

US 2011/0301693 A1  Dec. 8, 2011

Related U.S. Application Data

(62) Division of application No. 11/894,227, filed on Aug. 20, 2007, now Pat. No. 8,021,412.

(60) Provisional application No. 60/838,963, filed on Aug. 18, 2006.

(51) Int. Cl.
*A61F 2/82* (2006.01)
*A61F 2/06* (2006.01)

(52) U.S. Cl.
USPC .................. 623/1.31; 623/1.35; 623/1.15

(58) Field of Classification Search
USPC ....................... 623/1.15, 1.31, 1.35
IPC ................................ A61F 2/06, 2/82
See application file for complete search history.

*Primary Examiner* — Thomas Sweet
*Assistant Examiner* — Jason-Dennis Stewart
(74) *Attorney, Agent, or Firm* — Richard J. Godlewski

(57) ABSTRACT

A leg extension (10) for a stent grafting system to connect between an aortic graft and an iliac graft. The leg extension is a tubular body (12) of a biocompatible graft material with self-expanding stents connected along the length of the tubular body and the tubular body having a distal end with a connection region. The connection region has a flared stent defining an external frusto-conical surface to provide a connection arrangement to engage within an internally flared portion of an iliac graft.

20 Claims, 5 Drawing Sheets

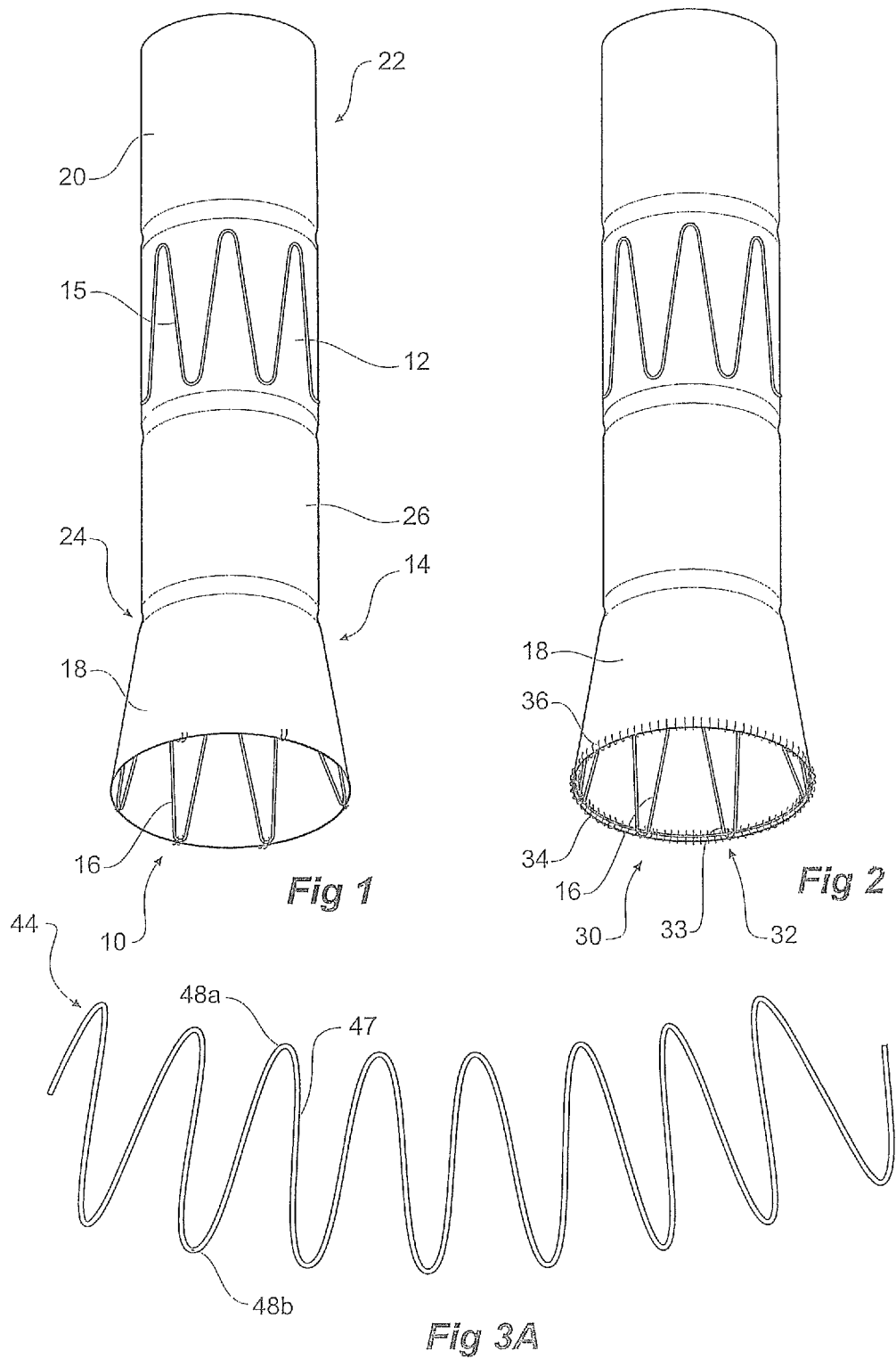

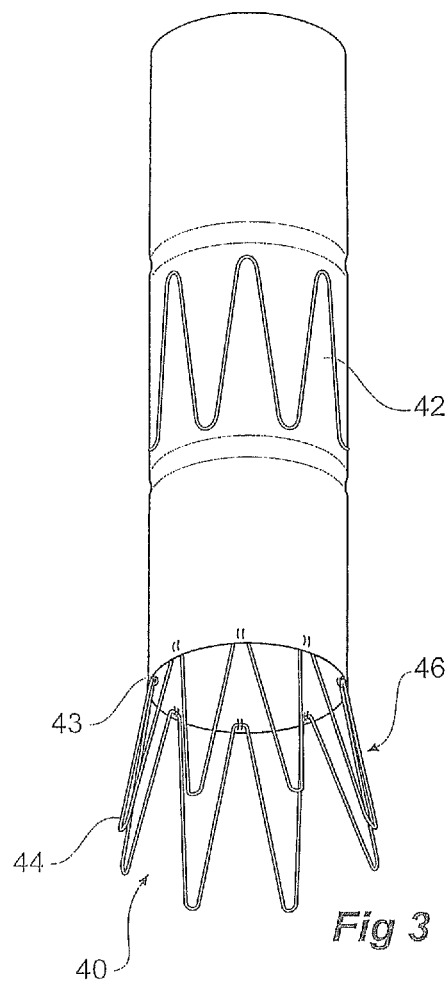
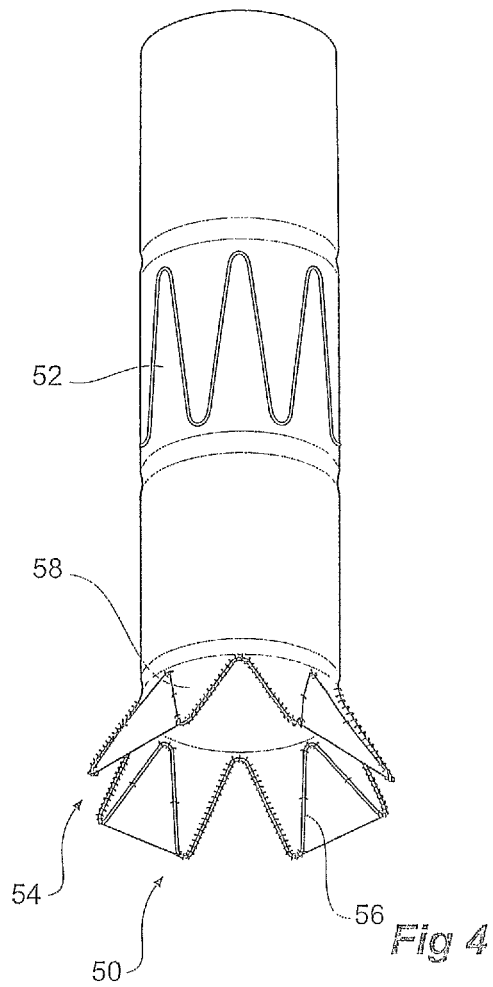
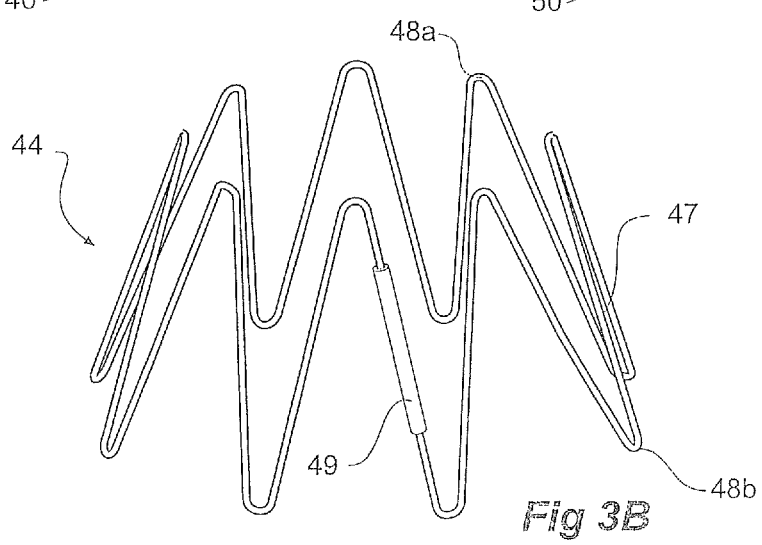

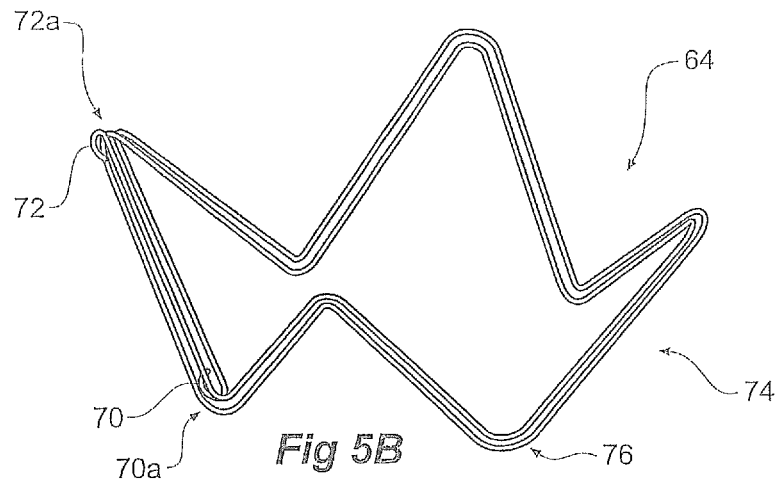
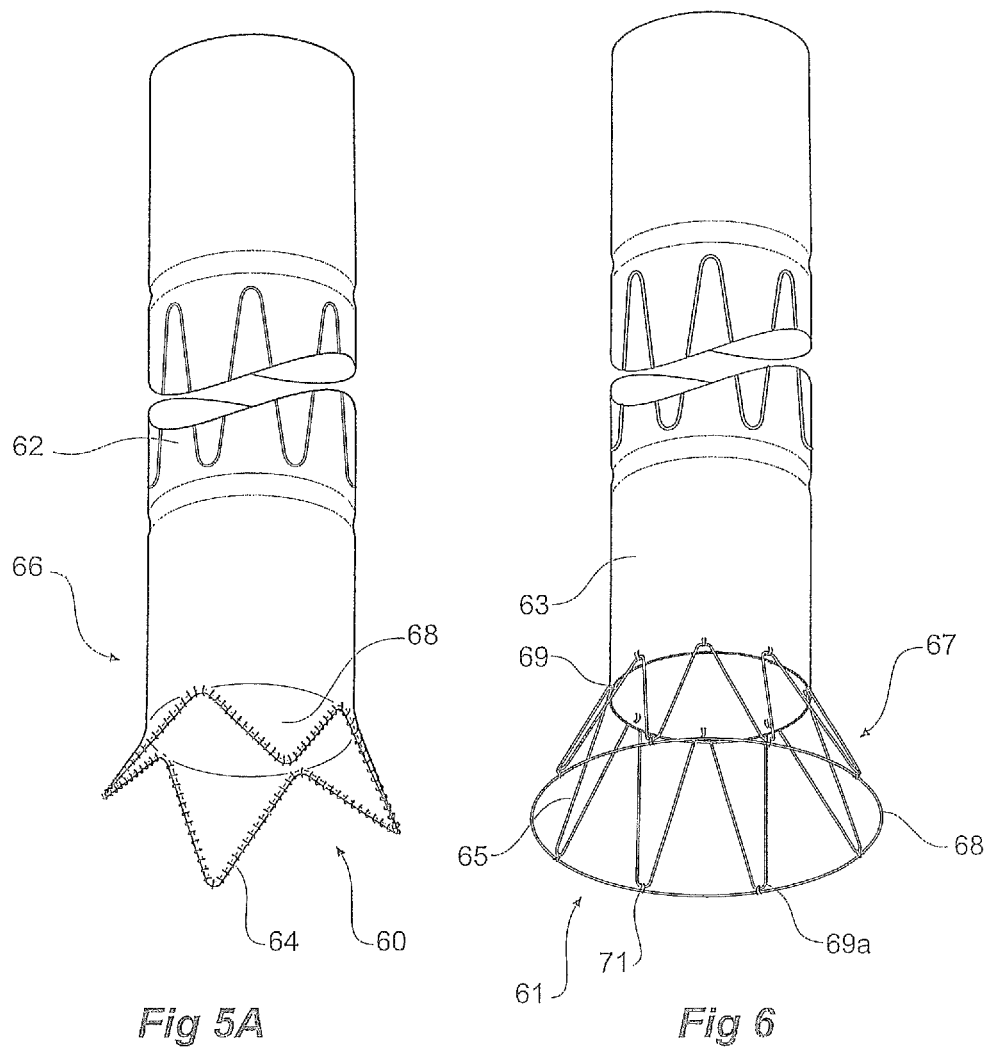
Fig 5B
Fig 5A
Fig 6

ILIAC EXTENSION WITH FLARED CUFF

CROSS-REFERENCE TO RELATED APPLICATIONS

This application is a divisional application that claims the benefit of priority under 35 U.S.C. §121 of U.S. patent application Ser. No. 11/894,227, filed Aug. 20, 2007, which is hereby incorporated by reference in its entirety.

INCORPORATION BY REFERENCE

The following co-pending patent applications are referred to in the following description:

PCT Patent Publication No. WO 98/53761 entitled "A Prosthesis and a Method Deploying a Prosthesis"

U.S. Provisional Patent Application Ser. No. 60/686,252, entitled "Iliac Artery Stent Graft" and U.S. Non-Provisional patent application Ser. No. 11/444,688 and Publication No. US-2006-0287704-A1.

U.S. Provisional Patent Application Ser. No. 60/838,776 filed on Aug. 18, 2006 herewith and entitled "Configuration of Branched Stent Grafts"

U.S. Patent Application Publication No. US-2003-01 99967-A1, and PCT Patent Publication No. WO 2003-0821 53 entitled "Bifurcated Branch Vessel Prosthesis"

U.S. Patent Application Publication No. US-2004-0082990-A1, and PCT Patent Publication No. WO 2004101 7867 entitled "Composite Prostheses"

U.S. Pat. No. 6,695,875 entitled "Endovascular Stent Graft"

TECHNICAL FIELD

This invention relates to a medical device and more particularly to a medical device for use in relation to endovascular surgery.

BACKGROUND OF THE INVENTION

There have been used bifurcated stent grafts for treating abdominal aortic aneurysms. Such stent grafts include a tubular body to extend in the aorta towards the renal arteries of a patient and usually a shorter leg and a longer leg with, once the bifurcated graft is deployed, an extension leg provided to extend down one iliac artery from the shorter leg with the longer leg extending down the other iliac artery.

In some cases of aneurysm, however, the aneurysm extends beyond the aortic bifurcation and down one at least of the iliac arteries. In such cases a separate branched iliac stent graft is deployed in the common iliac artery to allow for blood flow into the internal iliac and down the external iliac artery from the common iliac artery. There remains, however, the problem of connecting this branched iliac stent graft with the bifurcated stent graft in the aortic region.

It is to provide an extension for such an arrangement that the present invention is directed.

A particular problem with stent grafting in the common iliac region is that there is only a relatively short distance distally of the aortic bifurcation in which to make a connection and it is desirable that as secure as possible connection is provided.

Branched iliac stent grafts for use with the present invention are described in two U.S. Provisional Patent Applications. U.S. Provisional Patent Application Ser. No. 60/686, 252, filed Jun. 1, 2005 entitled "Iliac Artery Stent Graft" discloses a side branch stent graft having a main tubular body and a tubular side branch that is affixed into the main tubular so that the lumen of the side branch is in fluid communication with the lumen of the main body. External zig-zag stents are on the main body proximal and distal the side branch. At least one internal zig-zag stent is at the distal end of the main body. A reinforcing ring is around the proximal end of the main body and stitched thereto. This feature and other features disclosed in U.S. Provisional Patent Application Ser. No. 60/686,252 could be used with the present invention, and the disclosure of U.S. Provisional Patent Application Ser. No. 60/686,252 is herewith incorporated in its entirely into this specification.

U.S. Provisional Patent Application Ser. No. 60/838,776 filed on Aug. 18, 2006 herewith and entitled "Configuration of Branched Stent Grafts" discloses a stent graft with at least two adjacent fenestrations in a tubular body. A tube extends into the body from each of the at least two fenestrations. The tubes are joined and open into a single larger tube within the tubular body. The teaching of this patent specification is incorporated in the present application in its entirety.

Typical branched aortic bifurcation stent grafts are described in PCT Patent Publication No. WO 98153761 entitled "A Prosthesis And A Method and Means of Deploying A Prosthesis" discloses an introducer for a prosthesis which retains the prosthesis so that each end can be moved independently. These features and other features disclosed in PCT Patent Publication No. WO 98153761 could be used with the present invention and the disclosure of PCT Patent Publication No. WO 98153761 is herewith incorporated in its entirety into this specification.

U.S. patent application Ser. No. 10/396,676, filed Mar. 25, 2003, and published on Oct. 23, 2003, as U.S. Patent Application Publication No. US-2003-01 99967-A1, and PCT Patent Publication No. WO 2003-0821 53 entitled "Bifurcated Branch Vessel Prosthesis" disclose a stent graft with a fenestration in the tubular wall thereof. A tube extends from the fenestration into the main lumen and is in fluid communication therewith. An extension leg stent graft can be deployed from a branch vessel into the fenestration to seal in the tube. A flared guide associated with the fenestration can be provided interiorly or exteriorly. This feature and other features disclosed in U.S. Patent Application Publication No. US-2003-0199967-A1, and PCT Patent Publication No. WO 2003-0821 53 could be used with the present invention, and the disclosure of U.S. Patent Application Publication No. US-2003-01 99967-A1, and PCT Patent Publication No. WO 2003-0821 53 is herewith incorporated in its entirety into this specification.

U.S. Provisional Patent Application Ser. No. 60/405,769, filed Aug. 23, 2002, U.S. patent application Ser. No. 10/645, 095, filed Aug. 23, 2003, and published on Apr. 29, 2004, as U.S. Patent Application Publication No. US-2004-0082990-A1, and PCT Patent Publication No. WO 2004101 7867 entitled "Composite Prostheses" disclosed prostheses or stent grafts suitable for endoluminal deployment These prostheses and other features disclosed in U.S. Provisional Patent Application Ser. No. 60/405,769, U.S. patent application Ser. No. 10/645,095, and U.S. Patent Application Publication No. US-2004-0082990-A1, and PCT Patent Publication No. WO 20041077867 could be used with the present invention and the disclosure of U.S. Provisional Patent Application Ser. No. 60/405,769, U.S. patent application Ser. No. 10/645,095, and U.S. Patent Application Publication No. US-2004-0082990-A1, and PCT Patent Publication No. WO 2004/017867 is herewith incorporated in its entirely into this specification.

U.S. Pat. No. 6,695,875 entitled "Endovascular Stent Graft" discloses a main stent graft body and a separate attachment graft tube that extends proximally therefrom. The attachment graft tube has a proximal attachment stent for infrarenal attachment of the assembly to the aorta. These features and other features disclosed in U.S. Pat. No. 6,695,875 could be used with the resent invention and the disclosure of U.S. Pat. No. 6,695,875 is herewith incorporated in its entirety into this specification.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form therefore, although this may not necessarily be the broadest or only form, the invention is said to reside in a leg extension for a stent grafting system, the leg extension comprising a tubular body of a biocompatible graft material, the tubular body having a proximal end with an outside sealing surface, a plurality of self-expanding stents connected to the tubular body along the length thereof with at least one self-expanding stent within the tubular body at the proximal end and the tubular body having a distal end with a connection region, the connection region comprising a flared stent defining an external frusto-conical surface extending therefrom whereby to provide a connection arrangement to engage within an internally flared portion of an iliac graft, whereby the leg extension can connect between a pre-deployed branched iliac stent graft to a pre-deployed aortic bifurcation stent graft.

It will be seen that by this invention, there is provided an iliac extension stent graft which at its distal end can connect into an internally flared portion of a pre-deployed branched iliac graft and at its proximal end can extend up into a leg of a bifurcated aortic stent graft. By providing the proximal end with the outside sealing surface the proximal end of the stent graft can be variably positioned into the leg of a bifurcated stent graft to provide the required fluid connection between the pre-deployed branched iliac stent graft to the pre-deployed aortic bifurcation stent graft.

The flared stent is preferably a zigzag style Gianturco stent which may be formed from stainless steel, nitinol metal or other suitable materials.

The flared stent can in one embodiment be formed as self expanding stent comprising a resilient wire, the resilient wire comprising a plurality of struts and a bend between each strut, the stent as formed being substantially planar and in use being able to be formed into a substantially flared form with at least the first strut and the last strut overlapping.

Alternatively the flared stent can be formed from a resilient wire comprising a plurality of struts and a bend between each strut, the stent as formed being in a substantially planar form and the ends joined by welding or other technique.

In one form of the invention, the flared stent may be a bare stent extending from the distal end of the tubular body.

Alternatively the flared stent can be a covered stent comprising a cover of a biocompatible material.

In one form, the cover may be stitched along at least part of the line of the wire of the zigzag stent to in effect form a series of petals flaring out from the tubular body or the cover may extend between all or some of the distal bends of the flared stent.

There can be further included a ring stent at the distal end of the connection region fastened to the distal bends of the flared stent and/or to the cover of the connection region.

The proximal region with the outside sealing surface may be of a length of one, two or more stents within the tubular body. Similarly the distal sealing region may be of a length of one, two or more stents within the tubular body.

The biocompatible material from which the tubular body and the cover of the connection region is formed is preferably non-porous so that it does not leak or sweat under physiologic forces. The graft material is preferably made of woven or knitted polyester (Vascutek Ltd., Renfrewshire, Scotland, UK). Other biocompatible fabrics, non-woven materials and porous sheets may be used as the graft material. Examples of biocompatible polymers from which porous sheets can be formed include polyesters, such as poly(ethylene terephthalate), polylactide, polyglycolide and copolymers thereof; fluorinated polymers, such as PTFE, expanded PTFE and poly (vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. Preferably the porous sheet is made of one or more polymers that do not require treatment or modification to be biocompatible. The graft material may include a biocompatible polyurethane. Examples of biocompatible polyurethanes include THORALON® (Thoratec, Pleasanton, Calif.), BIOSPAN®, BIONATE®, ELASTHANE™, PURSIL™ and CARBOSIL™ (Polymer Technology Group, Berkeley, Calif.). As described in U.S. Patent Application Publication No. 2002/0065552 A1, incorporated herein by reference, THORALON® is a polyetherurethane urea blended with a siloxane-containing surface modifying additive. Specifically, the polymer is a mixture of base polymer BPS-215 and an additive SMA-300. The graft material may also include extracellular matrix materials. The "extracellular matrix" is a collagen-rich substance that is found in between cells in animal tissue and serves as a structural element in tissues. It is typically a complex mixture of polysaccharides and proteins secreted by cells. The extracellular matrix can be isolated and treated in a variety of ways. Following isolation and treatment, it is referred to as an "extracellular matrix material," or ECMM. ECMMs may be isolated from submucosa (including small intestine submucosa), stomach submucosa, urinary bladder submucosa, tissue mucosa, renal capsule, dura mater, liver basement membrane, pericardium or other tissues. Purified tela submucosa, a preferred type of ECMM, has been previously described in U.S. Pat. Nos. 6,206,931, 6,358,284 and 6,666,892 as a bio-compatible, non-thrombogenic material that enhances the repair of damaged or diseased host tissues. U.S. Pat. Nos. 6,206,931, 6,358,284 and 6,666,892 are incorporated herein by reference. Purified submucosa extracted from the small intestine ("small intestine submucosa" or "SIS") is a more preferred type of ECMM for use in this invention. Another type of ECMM, isolated from liver basement membrane, is described in U.S. Pat. No. 6,379,710, which is incorporated herein by reference. ECMM may also be isolated from pericardium, as described in U.S. Pat. No. 4,502,159, which is also incorporated herein by reference. Irrespective of the origin of the graft material, the graft material can be made thicker by making multi-laminate constructs, for example SIS constructs as described in U.S. Pat. Nos. 5,968,096; 5,955,110; 5,885,619; and 5,711,969. All of these references are incorporated herein by reference.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

BRIEF DESCRIPTION OF THE DRAWING

This then generally describes the invention but to assist with understanding, reference will now be made to the accompanying drawings which show preferred embodiments of the invention.

In the drawings:

FIG. 1 shows a first embodiment of leg extension for a stent grafting system according to the present invention;

FIG. 2 shows a further embodiment of a leg extension for a stent grafting system according to the present invention;

FIG. 3 shows a still further embodiment of a leg extension for a stent grafting system according to the present invention;

FIG. 3A shows detail of the flared stent of the embodiment of FIG. 3 in a laid flat configuration;

FIG. 3B shows detail of the flared stent of the embodiment of FIG. 3 in a frusto-conical configuration;

FIG. 4 shows a still further embodiment of a leg extension for a stent grafting system according to the present invention;

FIG. 5A shows an alternative embodiment of a leg extension for a stent grafting system according to the present invention;

FIG. 5B shows a form of flared stent useful for the connection region of the present invention and in particular the embodiment shown in FIG. 5A;

FIG. 6 shows an alternative embodiment of a leg extension for a stent grafting system according to the present invention;

DETAILED DESCRIPTION

Figure 7:
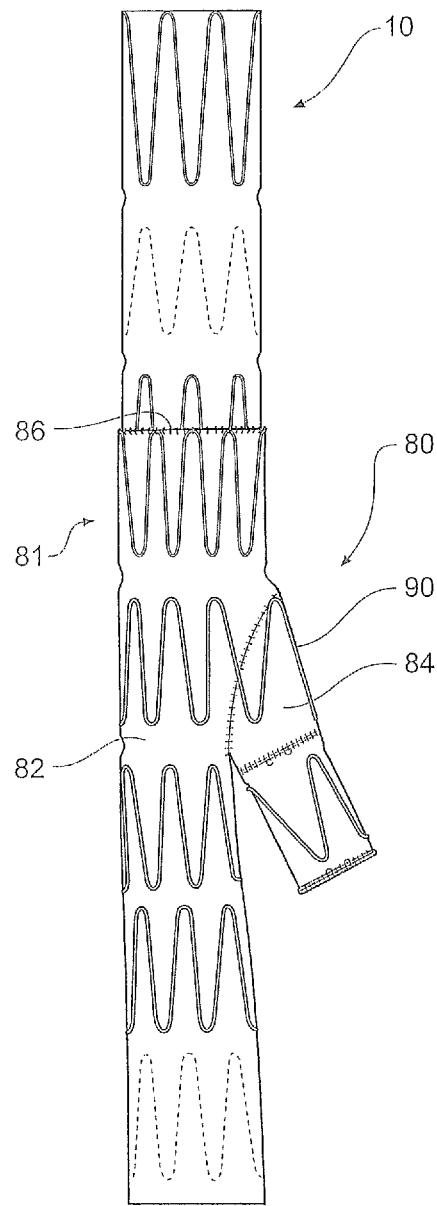
FIG. 7 shows an outside view of a connection between a branched iliac stent graft and a leg extension for a stent grafting system according to one embodiment of the invention.

Now looking more closely at the drawings and more particularly FIG. 1 it will be seen that a first embodiment of leg extension 10 for a stent grafting system according to the present invention comprises a tubular body 12 of a biocompatible graft material with the tubular body supported by self expanding stents 15. A connection region 14 comprising a flared stent 16 in this embodiment covered by a graft material cover 18 is at the distal end 24 of the leg extension 10.

The tubular body has a external proximal sealing surface 20 at its proximal end 22. The external proximal sealing surface has self expanding stents within the tubular body. The distal end 24 also has a sealing surface 26. The distal sealing surface has self expanding stents within the tubular body. The external proximal sealing surface 20 is arranged to seal within the leg of a bifurcated stent graft and the distal sealing surface 26 is adapted to seal within the proximal end of a branched iliac stent graft as will be discussed later.

Although the leg extension 10 has been shown as a particular length the length may vary and hence the number of intermediate stents 12 and the length of the tubular body can vary. There may be one, two or more self expanding stents within the sealing regions 20 and 26 and one, two or more self expanding stents 15 outside the tubular body 12 between the sealing regions 20 and 26.

FIG. 2 shows an alternative embodiment according to the present invention in which the leg extension 30 is substantially similar to that shown in FIG. 1 except that at the distal end 32 of the connection portion 18 there is a resilient ring 34 formed from a shape memory metal such as a nickel alloy nitinol metal stitched to the cover 18 by stitching 36 as well as being attached to the distal bends 33 of the flared stent 16. The resilient ring 34 assists in maintaining the flare in the connection portion and hence maintaining a connection as discussed above.

FIG. 3 shows a still further embodiment of a leg extension according to the present invention. In this embodiment the leg extension 40 comprises a tubular body 42 of a biocompatible graft material with an uncovered stent 44 providing the connection region 46. The uncovered stent 44 is a self expanding stent formed into a zig zag frusto conical configuration and is connected by the bends at the narrower end 43 of the stent to one end of the tubular body 42 such that it forms the flared configuration to comprise the connection region 46.

FIG. 3A shows detail of the flared stent of the embodiment of FIG. 3 in a laid flat configuration and FIG. 3B shows detail of the flared stent of the embodiment of FIG. 3 in a frusto-conical configuration. In this embodiment the stent 44 comprises struts 47, proximal bends 48a and distal bends 48b between the struts. The stent is initially formed into a flat configuration from a shape memory metal wire as shown in FIG. 3A and then after heat treatment is formed into a frusto-conical shape and has a welded, adhered or crimped scarf joint 49 to connect the ends of the wire into a continuous zig-zag shape.

FIG. 4 shows a still further embodiment of a leg extension according to the present invention. The leg extension 50 has a tubular body 52 of a biocompatible graft material and the connection region 54 comprises a zig zag stent 56 which is partially covered by a biocompatible graft material 58. In this embodiment alternate gaps between pairs of adjacent struts are left bare or uncovered.

FIG. 5A shows a still further embodiment of a stent graft according to the present invention. In this embodiment the leg extension stent graft 60 comprises a tubular body 62 of biocompatible graft material with a four lobed stent 64 fastened to the distal end 66. A covering of graft material 68 is stitched along the struts of the four lobed stent 64 to provide a petal effect. The stent 64 is a self expanding stent formed into a zig zag configuration from a shape memory metal such as the nickel alloy nitinol metal.

FIG. 5B shows the form of stent according to the embodiment of the invention shown in FIG. 5A. It will be seen that the stent 64 is formed from a single length of nitinol wire which commences at a loop 70 adjacent a bend 70a and forms a series of struts 74 with bends 76 in between them for two circuits before terminating at loop 72 adjacent to bend 72a with an overlap of one extra strut. The wire may be 0.15 mm diameter. The wire is formed into the four lobed frusto-conical shape and then heat treated to memorise that shape.

FIG. 6 shows a still further embodiment of a leg extension according to the present invention. In this embodiment the leg extension 61 comprises a tubular body 63 of a biocompatible graft material with an uncovered stent 65 providing the connection region 67. The uncovered stent 65 is a self expanding stent formed into a zig zag frusto conical configuration and is connected by the bends 69 at the narrower end of the stent to one end of the tubular body 63 such that it forms the flared configuration to comprise the connection region 67. To assist the stent 65 to maintain the flared configuration a ring 68 formed from a shape memory metal such as a nickel alloy nitinol wire is stitched to the outer bends 69a by stitching 71.

Figure 8:
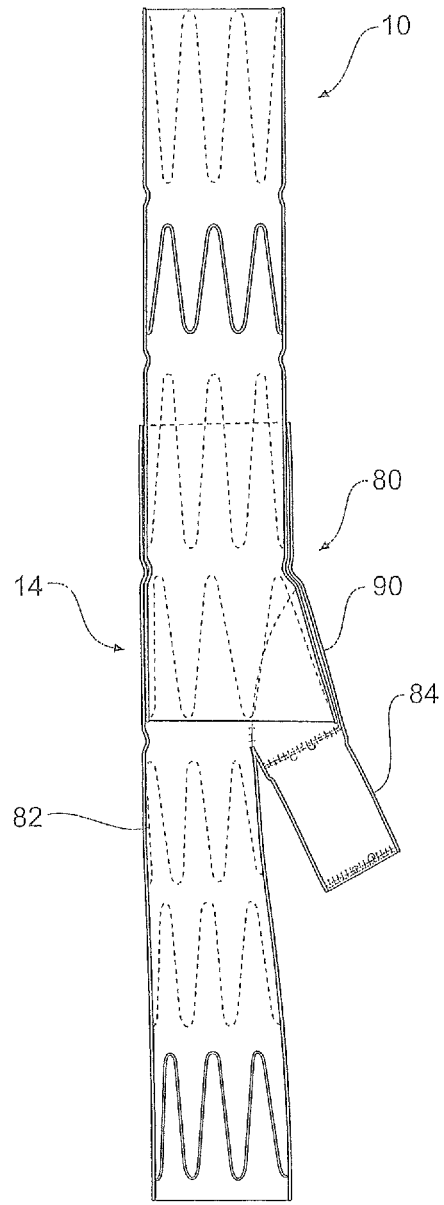
FIG. 8 shows a longitudinal cross sectional view of the connected components shown in FIG. 7.

FIG. 7 and FIG. 8 show one arrangement by which a leg extension according to the present invention is connected into a branched iliac stent graft. The branched iliac stent graft 80 comprises a tubular body 82 of a biocompatible graft material and a side arm 84 extending from the tubular body. At the proximal end of the tubular body is a ring reinforcement 86. The leg extension 10 of the type shown in FIG. 1 extends into the lumen of the iliac graft 80 at the proximal end 81 of the branched iliac stent graft 80 and extends into the tubular body 82 until the flared connection region 14 fits into the wider portion 90 where the side arm 84 extends from the tubular body 82. With the flared portion extending into the expanded portion 90 on the tubular body 82 a good connection between the two components is obtained which would be more difficult to pull out.

Figure 9:
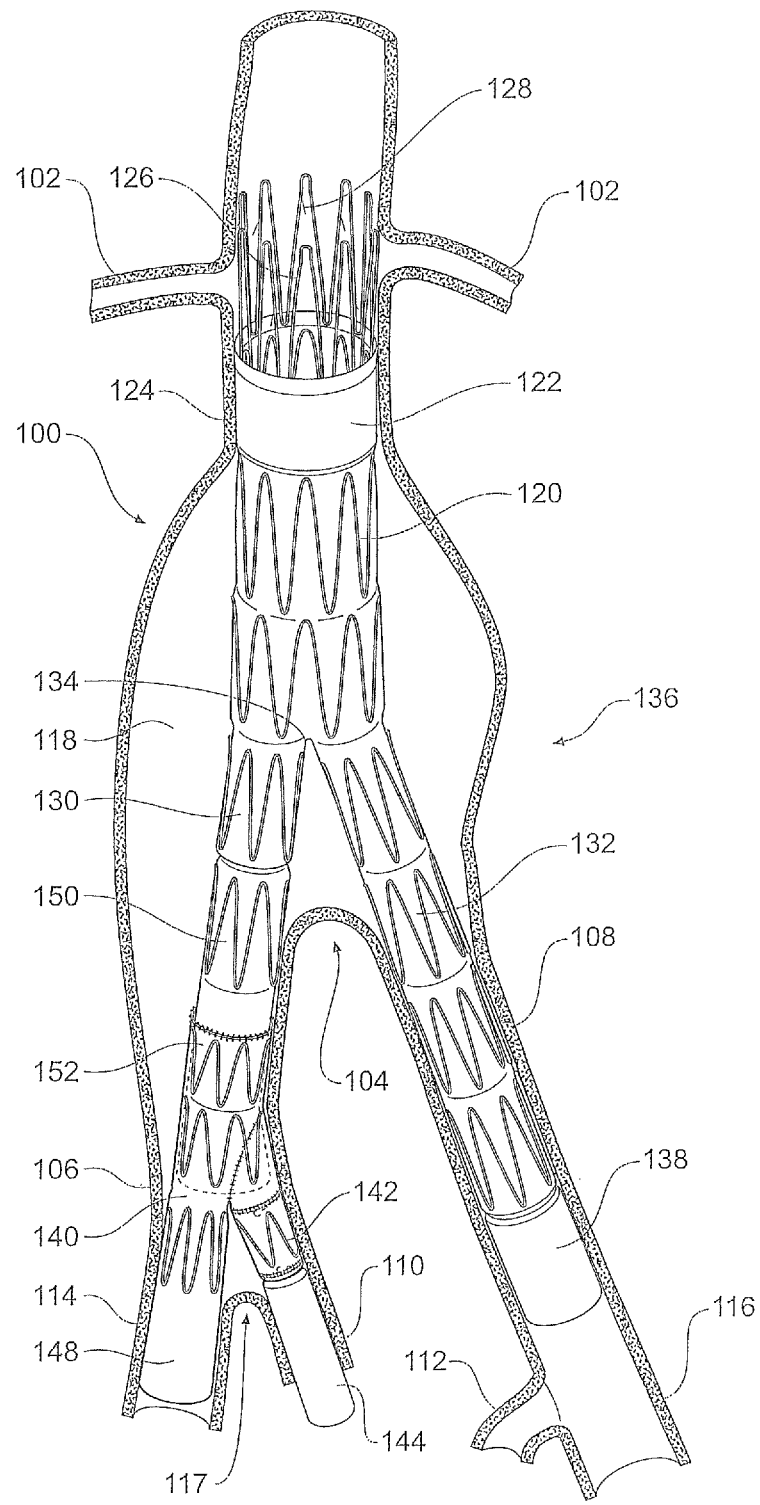
FIG. 9 shows a schematic view of a stent grafting system incorporating a leg extension according to the present invention assembled within the vasculature of a patient.

FIG. 9 shows a schematic view of the vasculature of a patient particularly showing the aorta and aortic bifurcation extending down towards the iliac arteries. The vasculature comprises an aorta 100 in the region between the renal arteries 102 and the aortic bifurcation 104. Common iliac arteries 106 and 108 extend from the aortic bifurcation 104. The common iliac arteries 106 and 108 each bifurcate into internal iliac arteries 110 and 112 and external iliac arteries 114 and 116 respectively. The aorta 100 has an aneurysm 118 which also extends down the common iliac artery 106 towards the iliac bifurcation 117.

To traverse the aneurysm a bifurcated aortic stent graft 120 has been deployed into the aorta 100. The proximal end 122 of the bifurcated stent graft 120 is engaged onto a non-aneurysed portion 124 of the aorta just distal of the renal arteries. To ensure good fixation the stent graft 120 includes a supra renal exposed stent 126 with barbs 128 engaging the wall of the aorta proximal of the renal arteries 102.

The stent graft 120 has a short leg 130 and a long leg 132 extending from a bifurcation 134 at its distal end 136. The long leg 132 has a sealing surface 138 at its distal end and this engages in a sealing manner into an non-aneurysed portion of the common iliac artery 108.

The aneurysm in the common iliac artery 106 requires the placement of an iliac stent graft 140 with a branch 142 from which a covered extension piece 144 can extend down the internal iliac artery 110. The distal end 148 of the iliac stent graft 140 engages in a sealing manner into an non-aneurysed portion of the external iliac artery 114.

The short leg 130 does not extend down to the aortic bifurcation and hence it is necessary to provide an iliac extension piece 150 which goes between the short leg 130 of the bifurcated aortic stent graft 120 and the proximal end 152 of the iliac stent graft 140. It is to the configuration of this iliac extension piece 150 that the present invention is directed.

The iliac extension piece 150 can be any of the embodiments shown in FIGS. 1 to 6 depending upon the requirements of a particular situation. The leg extension 150 extends into the lumen of the branched iliac graft 140 at the proximal end 152 of the branched iliac stent graft 140 and extends into the tubular body thereof until its flared connection region fits into the wider portion of the branched iliac stent graft where the side arm 142 extends from the tubular body. With the flared portion extending into the expanded portion on the tubular body a good connection between the two components is obtained even though there is a relatively short overlap.

In practice the order of placement of the various components of the stent grafting system in the case where there is an aneurysm which extends down into one of the common iliac arteries is as follows:

Deploy the branched iliac stent graft.
Deploy the internal iliac extension.
Deploy the bifurcated aortic stent graft.
Deploy the iliac extension piece according to the present invention.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A leg extension stent graft comprising a tubular body of a biocompatible graft material, the tubular body comprising a first end with an outside sealing surface, a plurality of self-expanding stents connected to the tubular body along the length thereof with at least one self-expanding stent within the tubular body at the first end, the tubular body comprising a second end comprising a connection region, the connection region comprising a flared stent defining an external frusto-conical surface extending from the second end of the tubular body, the flared stent comprising a self expanding stent being formed from a resilient wire, the flared stent comprising a frusto-conical configuration with a narrower first end and a wider second end, the narrower first end being connected to the second end of the tubular body, the resilient wire comprising a plurality of struts, a first bend between each strut at the first end of the flared stent and a second bend between each strut at the second end of the flared stent and further including a wire ring at the second end of the connection region, the wire ring being fastened to the second bends of the flared stent to assist the flared stent to maintain the frusto-conical configuration, the first bends being fastened to the second end of the tubular body, the flared stent thereby providing a connection arrangement when the connection region of the leg extension stent graft is engaged within an iliac stent graft.

2. A leg extension stent graft as in claim 1 wherein the flared stent is formed from a material selected from the group consisting of stainless steel and nitinol.

3. A leg extension stent graft as in claim 1 wherein the flared stent comprises a first strut, a last strut and plurality of struts therebetween and a bend between each strut, the stent, as formed, being substantially planar and in use being able to be formed into the frusto-conical configuration with at least the first strut and the last strut overlapping.

4. A leg extension stent graft as in claim 1 wherein the flared stent is a bare stent extending from the distal end of the tubular body.

5. A leg extension stent graft as in claim 1 wherein the flared stent further comprises a frusto-conical cover of a biocompatible graft material.

6. A leg extension stent graft as in claim 5 wherein the cover is stitched along at least part of the line of the wire of the stent to in effect form a series of petals flaring out from the tubular body.

7. A leg extension stent graft as in claim 5 wherein the cover is stitched along at least part of the line of the wire of the stent to in effect form a series of petals flaring out from the tubular body and the cover extends between some of the distal bends of the flared stent.

8. A leg extension stent graft as in claim 1 wherein the flared stent comprises a frusto-conical cover of a biocompatible graft material and an end of the frusto-conical cover is stitched to the wire ring.

9. A leg extension stent graft comprising a tubular body of a biocompatible graft material, the tubular body comprising a first end with an outside sealing surface, a plurality of self-expanding stents connected to the tubular body along the length thereof with at least one self-expanding stent within the tubular body at the first end, the tubular body comprising a second end comprising a connection region, the connection region comprising a flared stent defining an external frusto-conical surface extending from the second end of the tubular body, the flared stent comprising a self expanding stent being formed from a resilient wire, the flared stent comprising a frusto-conical configuration with a narrower first end and a wider second end, the narrower first end being connected to the second end of the tubular body, the resilient wire comprising a plurality of struts, a first bend between each strut at the first end of the flared stent and a second bend between each strut at the second end of the flared stent and further including a wire ring at the second end of the connection region, the wire ring being fastened to the second bends of the flared stent to assist the flared stent to maintain the frusto-conical configuration, the first bends being fastened to the second end of the tubular body, the flared stent further comprising a frusto-conical cover of a biocompatible graft material; the flared stent thereby providing a connection arrangement when the connection region of the leg extension stent graft is engaged within an iliac stent graft.

10. A leg extension stent graft as in claim 9 wherein the flared stent is formed from a material selected from the group consisting of stainless steel and nitinol.

11. A leg extension stent graft as in claim 9 wherein the flared stent comprises a first strut, a last strut and plurality of struts therebetween and a bend between each strut, the stent, as formed, being substantially planar and in use being able to be formed into the frusto-conical configuration with at least the first strut and the last strut overlapping.

12. A leg extension stent graft as in claim 9 wherein the cover is stitched along at least part of the line of the wire of the stent to in effect form a series of petals flaring out from the tubular body.

13. A leg extension stent graft as in claim 9 wherein the cover is stitched along at least part of the line of the wire of the stent to in effect form a series of petals flaring out from the tubular body and the cover extending between some of the distal bends of the flared stent.

14. A leg extension stent graft as in claim 9 wherein an end of the frusto-conical cover is stitched to the wire ring.

15. A leg extension stent graft comprising a tubular body of a biocompatible graft material, the tubular body comprising a first end with an outside sealing surface, a plurality of self-expanding stents connected to the tubular body along the length thereof with at least one self-expanding stent within the tubular body at the first end, the tubular body comprising a second end comprising a connection region, the connection region comprising a flared stent defining an external frusto-conical surface extending from the second end of the tubular body, the flared stent comprising a self expanding stent being formed from a resilient wire, the flared stent comprising a frusto-conical configuration with a narrower first end and a wider second end, the narrower first end being connected to the second end of the tubular body, the resilient wire comprising a plurality of struts, a first bend between each strut at the first end of the flared stent and a second bend between each strut at the second end of the flared stent and further including a wire ring at the second end of the connection region, the wire ring being fastened to the second bends of the flared stent to assist the flared stent to maintain the frusto-conical configuration, the first bends being fastened to the second end of the tubular body, the flared stent thereby providing a connection arrangement when the connection region of the leg extension stent graft is engaged within an iliac stent graft; the flared stent being formed from a single length of nitinol wire which commences at a first loop adjacent the first bend and then forming a series of struts with bends in between them for two circuits of the stent and terminating at a second loop adjacent to the second bend thereby providing an overlap of one extra strut.

16. A leg extension stent graft as in claim 9 wherein the flared stent is formed into the four lobed frusto-conical shape.

17. A leg extension stent graft as in claim 15 wherein the flared stent further comprises a frusto-conical cover of a biocompatible graft material.

18. A leg extension stent graft as in claim 17 wherein the cover is stitched along at least part of the line of the wire of the stent to in effect form a series of petals flaring out from the tubular body.

19. A leg extension stent graft as in claim 17 wherein the cover is stitched along at least part of the line of the wire of the stent to in effect form a series of petals flaring out from the tubular body and the cover extends between some of the distal bends of the flared stent.

20. A leg extension stent graft as in claim 15 wherein the flared stent comprises a frusto-conical cover of a biocompatible graft material and an end of the frusto-conical cover is stitched to the wire ring.

* * * * *